US009492487B2

(12) United States Patent
Garner et al.

(10) Patent No.: US 9,492,487 B2
(45) Date of Patent: Nov. 15, 2016

(54) MICROBIAL PRODUCT CONTAINING MULTIPLE MICROORGANISMS

(76) Inventors: Matthew Ryan Garner, Amarillo, TX (US); Joseph Flint, Ithaca, NY (US)

( * ) Notice: Subject to any disclaimer, the term of this patent is extended or adjusted under 35 U.S.C. 154(b) by 0 days.

(21) Appl. No.: 13/019,170

(22) Filed: Feb. 1, 2011

(65) Prior Publication Data
US 2011/0189132 A1  Aug. 4, 2011

Related U.S. Application Data

(60) Provisional application No. 61/300,294, filed on Feb. 1, 2010.

(51) Int. Cl.
*A61K 35/66* (2015.01)
*A61K 35/74* (2015.01)

(52) U.S. Cl.
CPC ............... *A61K 35/66* (2013.01); *A61K 35/74* (2013.01)

(58) Field of Classification Search
None
See application file for complete search history.

(56) References Cited

U.S. PATENT DOCUMENTS

2004/0096434 A1* 5/2004 Yamamoto et al. ....... 424/93.45
2008/0095890 A1* 4/2008 Watson .................. A23K 1/009
426/62

FOREIGN PATENT DOCUMENTS

| EP | WO 2006/108824 | * 10/2006 | ............. A61K 35/74 |
| WO | WO 92/12639 | * 8/1992 | ............. A01N 63/00 |
| WO | WO 2004/030624 | * 4/2004 | |

OTHER PUBLICATIONS

Ehrmann et al. (Characterization of lactobacilli towards their use as probiotic adjuncts in poultry. Journal of Applied Microbiology (2002), vol. 92, pp. 966-975).*
Biagi et al., Effect of a Lactobacillus animalis strain on composition and metabolism of the intestinal microflora in adult dogs; Veterinary Microbiology (2007), vol. 124, Issues 1-2, pp. 160-165.*

* cited by examiner

*Primary Examiner* — Alexander Kim
(74) *Attorney, Agent, or Firm* — Polsinelli PC

(57) ABSTRACT

Methods to reduce or inhibit populations of pathogenic bacteria in animals are disclosed. These methods include providing a number of administrations of probiotic microorganism compositions containing one or more strains or species of probiotic microorganisms. Routes of administration, dosage of administration and pathogenic organisms to be reduced or inhibited are also disclosed.

22 Claims, 5 Drawing Sheets

MICROBIAL PRODUCT CONTAINING MULTIPLE MICROORGANISMS

This application claims priority to U.S. provisional patent application 61/300,294 fined on Feb. 1, 2010, which is specifically incorporated by reference in its entirety without disclaimer.

BACKGROUND a. Field

The present disclosure relates generally to compositions and methods for manufacture and use of a multiple strain containing microbial product. More specifically, the disclosure relates to methods for improving animal health and/or productivity through the use of probiotic microorganisms.

b. Description of the Related Art

One of the larger economic burdens facing dairy farmers is the high cost of rearing and/or replacing heifers to maintain or increase herd size. A major factor contributing to the high cost of heifer replacement is the prevalence of diarrheal disease, known as scours, in livestock. Scours causes greater than 60% of all deaths associated with pre-weaned calves, and accounts for 6.2% of total calf losses. The prevalence of scours can vary dramatically (4.3% to 52.4%) depending on herd, diet, season, or "outbreak" occurrences. Estimates of scouring rates within a herd are difficult to obtain, though they are believed to between 15% and 35%. Nonetheless, it is agreed that diarrheal events comprise the largest health challenge to pre-weaned calves.

Diarrhea (scours) remains the predominant cause of mortality among dairy calves. There are multiple causes of scours including malabsorption and improper nutrition; however, infections by bacteria, viruses, and protozoa are the primary etiological agents. It is important to consider that scours in calves may be due to a number of concurrent gastrointestinal insults by numerous pathogens. Susceptibility to acute undifferentiated diarrhea can be largely determined by the quantity, quality, and administration time of colostrum.

The costs associated with scours are difficult to estimate; however, mortality alone represents a large expense, since, at birth, a heifer has an estimated value of $400-$600. Scours does not always result in death, but costs associated with treatment (e.g. electrolytes, antibiotics, veterinary services and associated labor) can be significant. In addition, animal sickness and death can negatively impact the morale of farm laborers and must be taken into consideration, though the financial costs of this cannot be readily quantified.

Serum immunoglobulin obtained from colostrum can offer some limited protection to calves from bacterial and viral infections. However, this protective effect begins to diminish <96 hours after birth, which could explain the high onset of viral scours 5-7 days following birth (Radostits 2000). Prophylactic antibiotics and vaccines administered to calves are frequent measures used to prevent scours in calves. While antibiotic administration can be effective against bacterial infections, antibiotics are ineffective against viruses and protozoa and, in fact, they can promote the development of viral or protozoal scours by diminishing the normal protective flora. Vaccinations can also confer protection against scours, however, the full protective immune response does not occur until after few weeks of administration. Despite some advances in prevention and treatment, the incidence of scours can vary wildly between dairy herds.

A major factor contributing to the onset of scours in calves is the practice of removing calves from their mother cows immediately after birth, and transporting them to facilities away from adult animals. The gastrointestinal tracts of mammals, including calves, are sterile at birth, but rapidly become colonized by microflora located near the mother's vagina and anus. Other bacteria begin to establish themselves when the neonate comes into contact with new objects (feed, dirt, gates, fences, handlers, etc.). Prior to the current practice of removing a calf from its mother, protective microflora would become established in the calf due to contact with the mother via licking, nursing, and grooming. Thus, one possible avenue to reduce the incidence and severity of scours includes manipulating the microbial flora of a calves' digestive tract.

It has long been known that a number of beneficial bacteria colonize the intestinal tracts of mammals and can promote the well being of the host. It has also been recognized for many years that the consumption of exogenous bacteria, often referred to as probiotics, can elicit beneficial effects upon a host. In humans, these probiotic bacteria have been shown to reduce the severity and duration of rotaviral-induced diarrhea, alleviate lactose intolerance, and enhance gastrointestinal immune function (Roberfroid 2000). Traditionally, food sources such as yogurt have been considered probiotic-carriers providing these health-promoting benefits. It is believed that the consumption of foods rich in probiotic bacteria, including lactic acid bacteria and bifidobacteria, leads to colonization of the human gastrointestinal tract of humans (Roberfroid 2000).

It is also well established that the addition of probiotic microorganisms to animal feed can improve animal efficiency and health. Specific examples include increased weight gain-to-feed intake ratio (feed efficiency), improved average daily weight gain, improved milk yield, and improved milk composition by dairy cows as described by U.S. Pat. Nos. 5,529,793 and 5,534,271. The administration of probiotic organisms can also reduce the incidence of pathogenic organisms in cattle, as reported by U.S. Pat. No. 7,063,836.

Researchers have demonstrated that the consumption of probiotics by animals used in food production can improve the efficiency of animal production. Probiotics may work by competitive exclusion in which live microbial cultures act antagonistically on specific organisms to cause a decrease in the numbers of that organism. U.S. Pat. No. 7,323,166. Mechanisms of competitive exclusion include production of antibacterial agents (bacteriocins) and metabolites (organic acids and hydrogen peroxide), competition for nutrients, and competition for adhesion sites on the gut epithelial surface. U.S. Pat. No. 7,323,166. Lactic acid bacteria are generally considered as food grade organisms and there are many potential applications of protective cultures in various foods. A number of different factors have been identified that contribute to the antimicrobial activity of lactic acid bacteria. These bacteria produce different antimicrobials, such as lactic acid, acetic acid, hydrogen peroxide, carbon dioxide and bacteriocins, which can inhibit pathogenic microorganisms.

Propionic acid is important in ruminal and intestinal fermentations and is a precursor to blood glucose synthesis (Baldwin 1983). Several examples are available that demonstrate the positive impact of feeding propionic acid-producing organisms to cattle. For example, U.S. Pat. Nos.

5,529,793 and 5,534,271, 6,455,063 and 6,887,489 demonstrate beneficial effects of propionic acid-producing bacteria upon cattle growth. Lactic acid bacteria (LAB) can inhibit pathogens in various food sources (Brashears et al., 2003). Lactic acid producing and lactate utilizing bacteria may also be helpful in inhibiting pathogenic growth in animals and improving the production of dairy products. U.S. Pat. No. 7,063,836. Lactic acid producing and lactate utilizing bacteria are beneficial for the utilization of feedstuffs by ruminants (U.S. Pat. Nos. 5,529,793 and 5,534,271) and have been fed to cattle to improve animal performance (Brashears et al., 2003).

Propionic acid is important in ruminal and intestinal fermentations and is a precursor to blood glucose synthesis (Baldwin 1983). Several examples are available that demonstrate the positive impact of feeding propionic acid-producing organisms to cattle. For example, U.S. Pat. Nos. 5,529,793 and 5,534,271, issued to Garner and Ware, along with U.S. Pat. Nos. 6,455,063 and 6,887,489, issued to Rehberger et al., teach of the beneficial effects that propionic acid-producing bacteria have upon cattle growth. Lactic acid bacteria (LAB) can inhibit pathogens in various food sources. Brashears et al., 2003. Lactic acid producing and lactate utilizing bacteria may also be helpful in inhibiting pathogenic growth in animals and improving the production of dairy products. U.S. Pat. No. 7,063,836. Lactic acid producing and lactate utilizing bacteria are beneficial for the utilization of feedstuffs by ruminants (U.S. Pat. Nos. 5,529, 793 and 5,534,271) and have been fed to cattle to improve animal performance. Brashears et al., 2003.

Bacteriocins are ribosomally synthesized extracellularly released bioactive peptides or peptide complexes which have bacteriocidal or bacteriostatic activity. The producer cells exhibit immunity to the action of its own bacteriocin. Bacteriocin producing strains can be identified in a deferred antagonism assay where colonies of putative producer cells are covered with a bacterial strain which is sensitive to the bacteriocins. After incubation, zones of inhibition are visible. Bacteriocins are known to inhibit foot borne pathogens such as *Clostridium botulinum, Enterococcus faecalis, Listeria monocytogenes* and *Staphylococcus aureus*.

Four general classes of bacteriocins have been characterized: 1) lantibiotics, 2) small <13 kDa hydrophobic heat stable peptides, 3) large >30 kDa heat labile proteins and 4) complex proteins that require additional carbohydrate or lipid moieties to attain antimicrobial activity. Lantibiotics are a family of membrane active peptides that contain a thio-ether amino acid known as lanthionine and β-methyl lanthionine as well as other modified amino acids such as dehydrated serine and threonine. A particular feature of lantibiotics is the presence of post translationally modified amino acid residues. One example of a lantibiotic is nisin. Bacteriocins which are small heat stable peptides do not contain modified amino acid residues. Large heat labile bacteriocins include helviticin-J and lactacins A and B.

A majority of bacteriocins produced by bacteria are lantibiotics or small hydrophobic heat stable peptides. Nisin, a lantibiotic is effective at inhibition of Gram-positive bacteria such as *Bacillus* and *Clostridium*. However, Nisin has demonstrated no effectiveness against Gram-negative bacteria. Among the small hydrophobic heat stable peptides, pediocins are frequently encountered and possess the ability to inhibit *Listeria monocytogenes*.

*Lactobacillus* genus includes the most prevalently administered probiotic bacteria (Flint and Angert 2005). *Lactobacillus* is a genus of more than 25 species of gram-positive, catalase-negative, non-sporulating, rod-shaped organisms (Heilig et al., 2002). *Lactobacillus* species ferment carbohydrates to form lactic acid as reported in U.S. Pat. No. 7,323,166. *Lactobacillus* species are generally anaerobic, non-motile, and do not reduce nitrate as reported in U.S. Pat. No. 7,323,166. *Lactobacillus* species are often used in the manufacture of food products including dairy products and other fermented foods as reported by Heilig et al., 2002 and U.S. Pat. No. 7,323,166. *Lactobacillus* species inhabit various locations including the gastrointestinal tracts of animals and intact and rotting plant material as reported by Heilig et al., 2002 and U.S. Pat. No. 7,323,166. *Lactobacillus* strains appear to be present in the gastrointestinal tract of approximately 70% of humans that consume a Western-like diet. Heilig et al., 2002. The number of *Lactobacillus* cells in neonates is approximately $10^5$ colony forming units (CFU) per gram CFU/g of feces. Heilig et al., 2002. The amount in infants of one month and older is higher, ranging from $10^6$ to $10^8$ CFU/g of feces. Heilig et al., 2002.

Lactic acid and products containing lactic acid have been found to enhance gains in the starting period of cattle (first 28 days) and reduce liver abscesses when given prior to the transition from a roughage diet to a feedlot diet. Various strains of *Lactobacillus acidophilus* have been isolated which restore and stabilize the internal microbial balance of animals. Manfredi et al., U.S. Pat. No. 4,980,164, is such a strain of *Lactobacillus acidophilus* which has been isolated for enhancing feed conversion efficiency. The *Lactobacillus acidophilus* strain of the Manfredi et al patent, has been designated strain BT1386 and received accession number ATCC No. 53545 from the American Type Culture Collection in Rockville, Md. Strain ATCC 53545 demonstrates a greater propensity to adhere to the epithelial cells of some animals which would increase their ability to survive, initiate and maintain a population within an animal intestine. Thus, the primary mode of action as previously understood relative to *Lactobacillus acidophilus* occurs post-ruminally.

The most common method used today to control pathogenic populations in livestock is through the use of antimicrobial compounds. While these are effective for short-term treatments, prolonged application of antimicrobial compounds leads to the evolution of antibiotic resistance in pathogenic organisms. The widespread occurrence of antibiotic resistant microorganisms is well known, some of the most common being methicillin resistant *Staphylococcus aureus* (MRSA) and vancomycin resistant enterococci (VRE). Bacteria are remarkably adaptable to deleterious environments with their abilities to rapidly reproduce and modify their genetic content. Thus, it is inevitable that after prolonged application of any method that disrupts or kills bacteria a population that is recalcitrant to its effects will eventually arise. It is not uncommon now in the medical environment that doctors often resort to using multiple antibiotics concurrently or in succession to eradicate pathogenic organisms.

As with antibiotics, bacteria can also become resistant to other biological treatments. For example, bacteriophages are able to reduce pathogen populations, but inevitably, a fraction of the targeted bacterial population is not infected. This small sub-population then rapidly reproduces and attains sizable population numbers. Some researchers have been able to overcome this by using multiple phages in a "cocktail" to reduce pathogen populations further than if only one was used. The premise behind including multiple phage is that different phage utilize different sites for attachment and infection of the host bacterium. While a cell can become resistant to one phage by modifying the phage attachment site, it is more difficult for the bacterium to modify two, three, or more attachment loci to evade all of the different phage in the cocktail.

Similar circumstances have been seen with the application of probiotic bacteria that are meant to inhibit or reduce the numbers of pathogenic bacteria within a gastrointestinal system. Some researchers have commented that significantly better animal performance and pathogen reductions were seen in treated animals early in their experiments, but the beneficial effects were no longer statistically different after prolonged application of the probiotic product. It is possible that the target populations were initially affected, but prolonged usage of the probiotic product led to the selection of bacterial populations that were not influenced by the application of the product. However, as seen with multiple phage application, it may be possible to avoid the adaptation of pathogens to probiotic treatment with the inclusion of multiple strains of bacteria.

There are numerous advantages for the inclusion of multiple strains of microorganisms in a microbial product. The potential advantages described below, whether working independently or concurrently, allow for a superior microbial product and enhanced benefits for the host.

Different microbial strains utilize certain nutrients more efficiently than others. The ability to use available nutrients in a gut environment is necessary for the microbe to produce antimicrobial compounds or to beneficially affect the host GI system. However, the nutrient availability is constantly changing because of animal behavior, different foods consumed, antibiotic use, energy requirements, or health of the animal. These fluctuations allow for different microbes to proliferate while other microbial populations diminish.

The use of different microbial strains also allows for the production of different microbial metabolites. Different metabolites have different effects upon pathogenic populations. Lactic acid is a powerful antimicrobial agent against some pathogens, while propionic acid is more effective against other populations. It should also be considered that just as metabolites produced from cells from the microbial product affect GI populations, endogenous microorganisms produce chemicals that may be inhibitory to some strains in the microbial product. The inclusion of different strains in a product increases the likelihood that the product will have a positive effect.

Additionally, the production of bacteriocins is known to influence bacterial populations. There is a large diversity of bacteriocins known and most target very specific microbial populations. Thus, a microbial product that contains multiple strains may be able to produce multiple bacteriocins and target different groups of pathogenic populations. Conversely, the intestinal tract contains a large diversity of bacteriocin producing bacteria. While some of the produced bacteriocins may affect one of the included strains, it is unlikely to affect all of the included microorganisms.

Another benefit of a multiple-strain containing product is the ability to target more than one pathogen population. Microbial pathogens are very diverse are require different methods to reduce or eliminate their populations. Thus, a product containing different microorganisms that are able to effect different pathogenic populations will result in an overall healthier system.

Different microorganisms positively influence the gastrointestinal system through different mechanisms. Including bacteria that work through different methods may result in a superior product. One strain may reduce pathogen populations, while another has an immunostimulative effect, while another produces micronutrients essential for the host. Interestingly, multiple strains may also provide synergistic effects upon the host or pathogen inhibition abilities. One strain alone may not be able to reduce certain populations, but the combination of two different strains working through different mechanisms can reduce pathogen populations.

Additionally, the use of multiple beneficial microorganisms can help overcome bacteriophages that infect and kill bacteria. Bacteriophages are very common in gastrointestinal systems and have profound effects upon the microbial community. Bacteriophages require specific sites on a cell to bind and infect. Thus, including multiple microorganisms in a product, the greater the likelihood that at least some populations from the product will evade bacteriophage attack and elicit beneficial effects upon the microbial community and host.

Some research has illustrated that a combination of different strains of beneficial probiotic bacteria can be used to treat discrete disorders. For example US Pub. No. 20070280910 describes a probiotic composition that includes three different bacterial species consisting of *Bacillus subtilis*, *Bacillus coagulans*, and *Enterococcus faecium* purportedly to treat autism, yeast infections, fybromyalgia, and irritable bowel syndrome. However, what is needed is a combination of probiotic bacteria compositions for administration to animals to eliminate or reduce gastrointestinal pathogens where a single probiotic bacteria species may be resisted by evolving pathogenic bacteria or phages found in the gastrointestinal environment. The novel approach described here meets these needs by providing a microbial composition that will decrease the incidence of pathogens, decrease animal mortality, improve animal health, and maximize animal efficiency.

SUMMARY

Certain embodiments of the present disclosure concern a method of inhibiting or reducing a population of pathogenic bacteria in or on an animal. In such embodiments the population of pathogenic bacteria may be on the skin of the animal, in the blood of the animal or in one or more organs of the animal. In specific embodiments, the disclosure concerns a method of inhibiting or reducing a population of pathogenic bacteria in the gastrointestinal tract of the animal.

In embodiments concerning the inhibition or reduction of a population of pathogenic bacteria, the method comprises providing to the animal two or more administrations of a composition comprising at least one probiotic microorganism.

In the embodiments of the disclosure, the probiotic microorganism may be any probiotic organism or any strain of a probiotic microorganism. In preferred embodiments, the composition to be administered comprises probiotic microorganisms which are lactic acid producing microorganisms. In specific embodiments the composition comprises *Enterococcus faecium*, *Bacillus licheniformis*, *Lactococcus lactis*, *Bacillus subtilis*, *Bifidobacterium adolescentis*, *Bifidobacterium animalis*, *Bifidobacterium bifidum*, *Bifidobacterium infantis*, *Bifidobacterium longum*, *Bifidobacterium thermophilum*, *Lactobacillus acidophilus*, *Lactobacillus agilis*, *Lactobacillus alactosus*, *Lactobacillus alimentarius*, *Lactobacillus amylophilus*, *Lactobacillus amylovorans*, *Lactobacillus amylovorus*, *Lactobacillus animalis*, *Lactobacillus batatas*, *Lactobacillus bavaricus*, *Lactobacillus bifermentans*, *Lactobacillus bifidus*, *Lactobacillus brevis*, *Lactobacillus buchnerii*, *Lactobacillus bulgaricus*, *Lactobacillus catenaforme*, *Lactobacillus casei*, *Lactobacillus cellobiosus*,

*Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus sobrius, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaceus, Streptococcus cremoris, Streptococcus diacetylactis, Streptococcus faecium, Streptococcus intermedius, Streptococcus lactis, Streptococcus thermophilus, Propionibacterium freudenreichii, Propionibacterium acidipropionici, Propionibacterium jensenii, Propionibacterium thoenii, Propionibacterium cyclohexanicum, Propionibacterium granulosum, Propionibacterium microaerophilum, Propionibacterium propionicum, Propionibacterium acnes, Propionibacterium australiense, Propionibacterium avidum* or a combination thereof. In other embodiments, the composition comprises one or more different strains of the aforementioned species of probiotic microorganisms.

In embodiments of the present disclosure wherein populations of pathogenic bacteria are to be reduced or inhibited, the pathogenic bacteria may be any pathogenic bacteria known to afflict animals, such as mammals. In particular embodiments the pathogenic bacteria is *Staphylococcus aureus, Staphylococcus epidermis, Staphylococcus saprophyticus, Streptococcus pyogenes, Streptococcus pneumoniae, Streptococcus agalactiae, Enterococcus faecalis, Corynebacterium diptheriae, Bacillus anthracis, Listeria monocytogenes, Clostridium perfringens, Clostridium tetanus, Clostridium botulinum, Clostridium difficile, Neisseria meningitidis, Neisseria gonorrhoeae, Escherichia coli, Salmonella typhimurium, Salmonella cholerasuis, Salmonella enterica, Salmonella enteriditis, Yersinia pestis, Yersinia pseudotuberculosis, Yersinia enterocolitica, Vibrio cholerae, Campylobacter jejuni, Campylobacter fetus, Helicobacter pylori, Pseudomonas aeruginosa, Pseudomonas mallei, Haemophilus influenzae, Bordetella pertussis, Mycoplasma pneumoniae, Ureaplasma urealyticum, Legionella pneumophila, Treponema pallidum, Leptospira interrogans, Borrelia burgdorferi, Mycobacterium tuberculosis, Mycobacterium leprae, Chlamydia psittaci, Chlamydia trachomatis, Chlamydia pneumoniae, Rickettsia ricketsii, Rickettsia akari, Rickettsia prowazekii, Brucella abortus, Brucella melitens, Brucella suis, Francisella tularensis* or combinations thereof. Additionally, in certain embodiments, the pathogenic bacteria include one or more strains of one of the aforementioned pathogenic bacteria. For example, it is contemplated that the methods of the present disclosure may be used to reduce or inhibit a population of the O157:H7 strain of *Escherichia coli*.

In embodiments of the present disclosure wherein two or more administrations of a composition comprising at least one probiotic microorganism is contemplated, specific embodiments contemplate that each composition differs from the other or previously administered compositions by at least one species or strain of probiotic microorganism.

In embodiments of the present disclosure wherein an administration of probiotic microorganisms is contemplated, the number of microorganisms per administration may be any amount capable of providing some inhibition or reduction of a population of pathogenic bacteria. In specific embodiments the number of microorganisms per administration is between $1 \times 10^3$ and $1 \times 10^9$ microorganisms. In preferably the number of microorganisms in an administration is at approximately $1 \times 10^6$ microorganisms.

The administrations may be timed such that an administration is separated by 1, 2, 3, 4, 5, 6, 7, 8, 9, 10, 11, 12, 13, 14, 15, 16, 17, 17, 19, 20, 21, 22 or 23 hours or 1, 2, 3, 4, 5, or 6 days or 1, 2 or 3 weeks or 1 month or some duration in between. In preferred embodiments the administrations are separated by 1 to 7 days. In specific embodiments, the administrations are separated by 1 day.

The administration may be oral, rectal, or via injection. In preferred embodiments, the administrations are oral administrations. In embodiments wherein the administrations are oral administrations, the composition comprising one or more probiotic bacteria may be mixed with animal feed or mixed with animal drinking water. In such embodiments, the composition or compositions may be formulated as a liquid formulation for administration, or as a freeze dried formulation, or as a gel formulation or as a spore formulation.

Additional steps in inhibiting or reducing population of pathogenic bacteria in an animal include assessing the presence of pathogenic bacteria in the gastrointestinal tract of the animal between administrations. In more specific embodiments, the animal is assessed for the presence of pathogenic bacteria, for strain of pathogenic bacteria, species of pathogenic bacteria and number of pathogenic bacteria present. In specific embodiments, this assessment is done by examining the feces of the animal.

Consistent with long standing patent law, the words "a" and "an" denote "one or more," when used in the text or claims of this specification in conjunction with the word "comprising" or where the context of the usage suggests that, from either a grammatical or scientific standpoint, these words should so denote.

DETAILED DESCRIPTION a. Definitions

Figure 1:
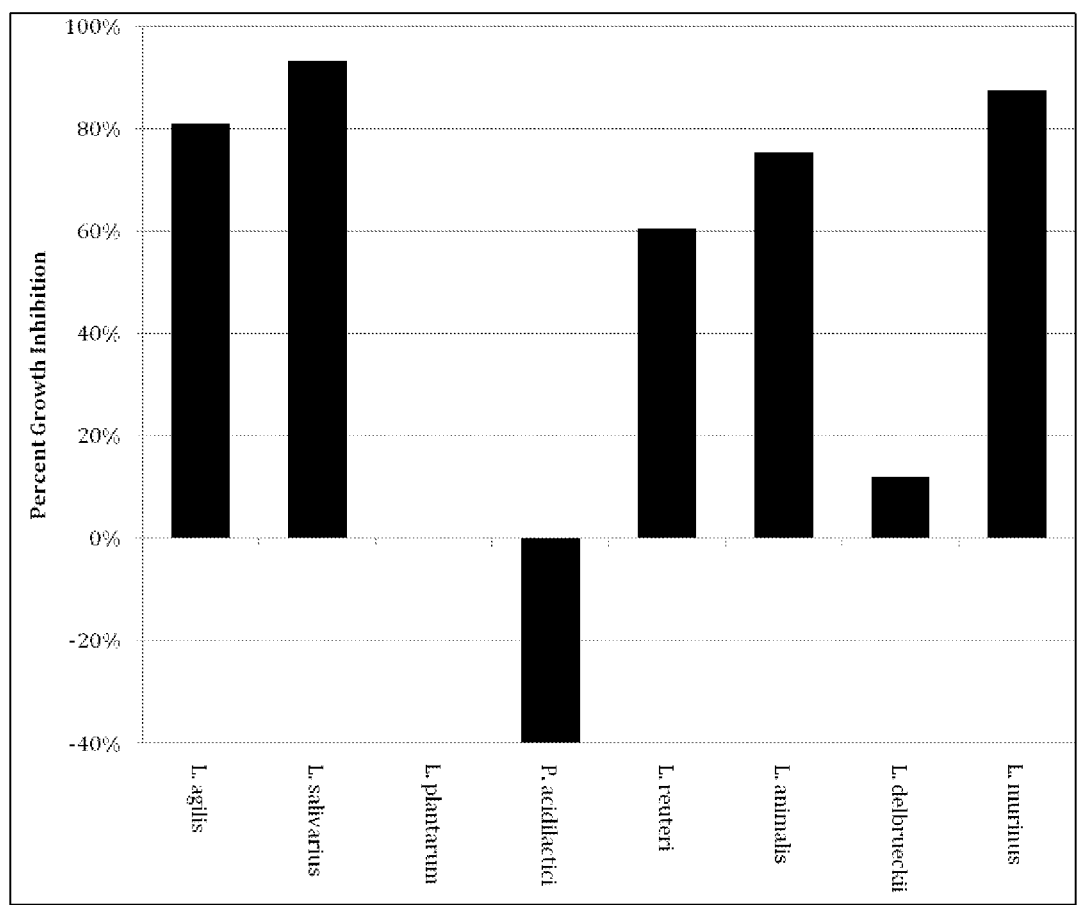
FIG. 1 is a bar graph illustrating the growth inhibition of *E. coli* strain CKYL1 by various lactic acid producing bacteria.

Before describing the present disclosure in detail, it is to be understood that this disclosure is not limited to particular compositions or biological systems, which can, of course, vary. It is also to be understood that the terminology used herein is for the purpose of describing particular embodiments only, and is not intended to be limiting. Also, throughout this specification, various publications are referenced. The disclosures of these publications in their entireties are hereby incorporated by reference into this application in order to more fully describe the state of the art to which the disclosed subject matter pertains. The references disclosed are also individually and specifically incorporated by reference herein for the material contained in them that is discussed in the sentence in which the reference is relied upon.

Unless defined otherwise, all technical and scientific terms used herein have the same meaning as commonly understood by one of ordinary skill in the art to which the disclosure belongs. Although any methods and materials similar or equivalent to those described herein can be used in the practice or testing of the present disclosure, the preferred methods and materials are now described.

In this specification and the claims that follow, reference will be made to a number of terms which may be considered to have the following meanings:

By "reduce" or other forms of the word, such as "reducing" or "reduction," may in certain instances refer to lowering of an event or characteristic (e.g., microorganism growth or survival). It is understood that this is typically in relation to some standard or expected value, in other words it is relative, but that it is not always necessary for the standard or relative value to be referred to. For example, "reduces the population of bacteria" in certain instances may refer to lowering the amount of bacteria relative to a standard or a control.

By "treat" or other forms of the word, such as "treated" or "treatment," may, in certain instances mean to administer a composition or to perform a method in order to reduce, prevent, inhibit, break-down, or eliminate a particular characteristic or event (e.g., microorganism growth or survival).

The term "viable cell" may in certain instances mean a microorganism that is alive and capable of regeneration and/or propagation, while in a vegetative, frozen, preserved, or reconstituted state.

The term "viable cell yield" or "viable cell concentration" may, in certain instances refer to the number of viable cells in a liquid culture, concentrated, or preserved state per a unit of measure, such as liter, milliliter, kilogram, gram or milligram.

The term "cell preservation" in certain instances may refer to a process that takes a vegetative cell and preserves it in a metabolically inert state that retains viability over time. As used herein, the term "product" in certain instances may refer to a microbial composition that can be blended with other components and contains specified concentration of viable cells that can be sold and used.

As used herein, the terms "microorganism" or "microbe" may in certain instances refer to an organism of microscopic size, to a single-celled organism, and/or to any virus particle.

Our definition of microorganism includes Bacteria, Archaea, single-celled Eukaryotes (protozoa, fungi, and ciliates), and viral agents. The term "microbial" is used herein to describe processes or compositions of microorganisms, thus a "microbial-based product" is a composition that includes microorganisms, cellular components of the microorganisms, and/or metabolites produced by the microorganisms.

Microorganisms can exist in various states and occur in vegetative, dormant, or spore states. Microorganisms can also occur as either motile or non-motile, and may be found as planktonic cells (unattached), substrate affixed cells, cells within colonies, or cells within a biofilm.

The term "prebiotic" in certain instances may refer to food ingredients that are not readily digestible by endogenous host enzymes and confer beneficial effects on an organism that consumes them by selectively stimulating the growth and/or activity of a limited range of beneficial microorganisms that are associated with the intestinal tract.

The term "probiotic" in certain instances may refer to one or more live microorganisms that confer beneficial effects on a host organism. Benefits derived from the establishment of probiotic microorganisms within the digestive tract include reduction of pathogen load, improved microbial fermentation patterns, improved nutrient absorption, improved immune function, aided digestion and relief of symptoms of irritable bowel disease and colitis.

The term "synbiotic" in certain instances may refer to a composition that contains both probiotics and prebiotics. Synbiotic compositions are those in which the prebiotic compound selectively favors the probiotic microorganism.

The term "gastrointestinal tract" in certain instances may refer to the complete system of organs and regions that are involved with ingestion, digestion, and excretion of food and liquids. This system generally consists of, but not limited to, the mouth, esophagus, stomach and or rumen, intestines (both small and large), cecum (plural ceca), fermentation sacs, and the anus.

The term "pathogen" in certain instances may refer to any microorganism that produces a harmful effect and/or disease state in a human or animal host.

The term "fermentation" in certain instances may refer to a metabolic process performed by an organism that converts one substrate to another in which the cell is able to obtain cellular energy, such as when an organism utilizes glucose and converts it to lactic acid or propionic acid. Many of the end-substrates formed in fermentation processes are volatile fatty acids.

The term "volatile fatty acids" in certain instances may refer to short-chain fatty acids containing six or fewer carbon atoms and at least one carboxyl group. Some examples of VFAs include, but are not limited to: lactic acid, acetic acid, propionic acid, butyric acid, isobutyric acid, valeric acid, and isovaleric acid, which are products of microbial fermentation within the digestive tracts of animals. Volatile fatty acids can be absorbed through the intestines of animals and used as an energy or carbon source. Microbes produce VFAs based on available substrates and also rely upon VFAs for energy and carbon sources.

The term "lactic acid" in certain instances may refer to a byproduct of glucose fermentation resulting in a three-carbon acid with the chemical formula $C_3H_6O_3$. This includes, but is not limited to, lactic acid derived from specific strains of bacteria or lactic acid derived from other types of organisms. Lactic acid can be microbialstatic, microbialcidal, bacteriostatic, bacteriocidal or bacteriolytic; these concepts are known to skilled persons. "Lactic acid producing" refers to any organism that generates lactic acid.

The term "bacteriocin(s)" in certain instances may refer to (poly) peptides and proteins that inhibit one or more microbial species. This includes, but is not limited to, (poly) peptides or proteins that were derived from specific strains of bacteria or (poly) peptides that are derived from other types of organisms. The bacteriocin can be microbialstatic, microbialcidal, bacteriostatic, bacteriocidal, or bacteriolytic; these concepts are known to skilled persons. For the treatment of produce and other food products the bacteriocin is preferably microbialcidal or bacteriocidal. "Bacteriocin producing" in certain instances may refer to any organism that generates bacteriocins.

As used herein, "hydrogen peroxide" in certain instances may refer to a byproduct of oxygen metabolism that has the chemical formula $H_2O_2$. This includes, but is not limited to, hydrogen peroxide derived from specific strains of bacteria or hydrogen peroxide derived from other types of organisms. Hydrogen peroxide can be microbialstatic, microbialcidal, bacteriostatic, bacteriocidal or bacteriolytic; these concepts are known to skilled persons. "Hydrogen peroxide-producing" refers to any organism that generates hydrogen peroxide.

As used herein, the term "synergistic" in certain instances may refer to a property wherein the combined result of two effects is greater than would be expected if the two effects were added together. The term "synergistically" is used to describe a synergistic effect.

As used herein, the phrase "foregut fermentor" in certain instances may refer to an animal having an anatomical compartment in the alimentary canal that is positioned anterior to the stomach that is used for microbial fermentation and digestion of ingested materials. Ruminal fermentors are considered foregut-fermenting organisms.

As used herein, the phase "ruminal fermentor" or "rumen fermenting" in certain instances may refer to an animal having a large, multi-compartmented section of the digestive tract, called a rumen, which is positioned between the esophagus and the anus. Rumen are very complex ecosystems that support microbial fermentation of cellulose, plant matter, and other ingested materials. Ruminal-fermentors may also be termed "cranial fermentors" or "ruminants". Some examples of rumen-fermenting organisms include cattle, sheep, goats, camels, llama, bison, buffalo, deer, wildebeest, antelope, etc.

As used herein, the phrase "hindgut fermentor" in certain instances may refer to an animal having a complex large intestine that may or may not include specialized fermentation chambers that can include a cecum or blind sac, that is positioned posterior to the stomach in the alimentary canal. Cecal fermentors and intestinal fermentors are both considered hindgut-fermenting organisms.

As used herein, the phrase "cecal fermentor" in certain instances may refer to an animal having a complex large intestine that includes a cecum or a blind sac along the digestive tract. The cecum of a cecal fermentor forms a distinct chamber, which is the primary site of microbial fermentation of cellulose, plant matter, or other ingesta. A cecal-fermentor may also be referred to as "caudal fermentor". Cecal-fermentors include horses, elephants, rabbits, mice, rats, guinea pigs, etc.

As used herein, the term "intestinal fermentor" in certain instances may refer to an animal that does not primarily rely upon microbial fermentation of ingesta in a rumen or large cecum. In the digestive tracts of intestinal fermentors, microbial fermentation occurs primarily within the large intestine or colon. Intestinal fermentors include chickens, pigs, humans, etc.

As used herein, the term "monogastric" in certain instances may refer to an animal having a single, simple (single chambered) stomach. Typically, cecal fermentors and intestinal-fermentors are monogastric animals. Some examples of monogastric animals include horses, chickens, pigs, humans, etc.

As used herein, the term "polygastric" in certain instances may refer to an animal having a multiple, complex (multi-chambered) stomachs. Ruminal fermentors are polygastric animals.

As used herein, the phrase "pre-gastric fermentation" in certain instances may refer to microbial fermentation that occurs before the food reaches a 'true' stomach, which is generally the site of gastric acid and digestive enzyme secretion. Ruminants are pre-gastric fermentors.

As used herein, the phrase "post-gastric fermentation" in certain instances may refer to microbial fermentation that occurs after food passes through a stomach, which is generally the site of gastric acid and digestive enzyme secretion. Hindgut fermentors, including cecal fermentors and intestinal fermentors, utilize post-gastric fermentation.

As used herein, the term "herbivore" in certain instances may refer to an animal that exclusively consumes plant material.

As used herein, the term "omnivore" in certain instances may refer to an animal that consumes both plant and animal material.

As used herein, the term "carnivore" in certain instances may refer to an animal that exclusively consumes animal material.

As used herein, "digesta" in certain instances may refer to food or any other material that enters the alimentary canal and undergoes, completely or partially, through the process of being digested or broken down into smaller components.

b. Introduction

The present disclosure discloses a novel synbiotic composition comprised of multiple probiotic microorganisms. The present disclosure can be adjusted to provide beneficial effects to many types of animals, including ruminal fermentors, cecal fermentor and intestinal fermentors. In one preferred embodiment, the probiotic formulation supplemented with prebiotic compounds is fed to ruminal fermentors to reduce scours events and improve animal health. Ruminal fermentors that might benefit from the present disclosure include but are not limited to: cattle, sheep, goats, camels, llama, bison, buffalo, deer, wildebeest, antelope, and any other pre-gastric fermentor. In another embodiment, the probiotic formulation supplemented with prebiotic compounds is fed to cecal fermentors to reduce scours events and improve animal health. Cecal fermentors that might benefit from said disclosure include but are not limited to: horses, ponies, elephants, rabbits, hamsters, rats, hyraxes, guinea pigs, and any other post-gastric fermentor that using the cecum as the primary location of fermentative digestion. In another embodiment, the probiotic formulation supplemented with prebiotic compounds is fed to intestinal fermentors to reduce scours events and improve animal health. Intestinal fermentors that might benefit from said disclosure include but are not limited to: humans, pigs, chickens, and other post-gastric fermentor using the large intestine as the primary location of fermentative digestion. In each case, the synbiotic composition is packaged in format that ensures survival of both the probiotic and prebiotic components into the gastrointestinal system of the animal.

One object of the present disclosure to provide a novel composition that will reduce mortality and morbidity and/or improve animal health and/or productivity. A further object of the present disclosure to provide a composition that will be used once, periodically or on a continual basis to reduce the incidence and severity of scours and/or improve animal health. Still further, another object of the present disclosure is to provide a composition that is durable and easy to apply to animal feed or other easily ingestible materials.

The novel composition, which comprises mixtures of probiotic microorganisms, facilitates the production of lactic acid, which inhibits the growth of pathogenic organisms during digestive fermentation. The composition comprises a mixture of lactic acid-producing bacteria in combination with a lactic acid-utilizing and propionic acid-producing bacteria. In some embodiments, the composition is mixed with colostrum or milk replacers. In other embodiments the mixture is applied to milk or water administered to the calves. Animals can be treated with one or more viable microorganisms in combination with prebiotic compounds to improve animal efficiency and/or health. Additive, or more preferably super-additive or more preferably synergistic effects can be achieved with the administration of one or more microbial species and/or strains. Animals can be treated once, multiple times, or continuously in a day.

It is preferred that the probiotic mixture could contain any number of microorganisms and or microbial components and/or metabolites. Examples of bacterial species that could be used for the probiotic mixture include but are not limited to the group consisting of: *Enterococcus faecium, Bacillus licheniformis, Lactococcus lactis, Bacillus subtilis, Bifidobacterium adolescentis, Bifidobacterium animalis, Bifidobacterium bifidum, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus sobrius, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaceus, Streptococcus cremoris, Streptococcus discetylactis, Streptococcus faecium, Streptococcus intermedius, Streptococcus lactis, Streptococcus thermophilus, Propionibacterium* spp., *Propionibacterium freudenreichii, Propionibacterium acidipropionici, Propionibacterium jensenii, Propionibacterium thoenii, Propionibacterium cyclohexanicum, Propionibacterium granulosum, Propionibacterium microaerophilum, Propionibacterium propionicum, Propionibacterium acnes, Propionibacterium australiense, Propionibacterium avidum* and strains and/or combinations thereof. Furthermore, a lactic acid producing microorganism can be a strain of *Lactobacillus* spp., such as the MRL1, M35, LA45, LA51, L411, NPC 747, NPC 750, D3, and L7 strains. Examples of a lactic acid-utilizing and/or propionic acid-producing organism include the *Propionibacterium* spp. strains PF24, P5, P63, P1, and MRP1.

c. Formulations

In certain aspects of the disclosure contemplate a carrier formulation for the probiotic microorganisms. In certain aspects of the disclosure, the carrier may be any number of different percentages (weight per weight, weight per volume, or volume per volume) of the final product. The carrier can comprise any amount of about 99.9%, about 95%, about 90%, about 80%, about 70%, about 60% about 50%, about 40%, about 30% and so on. The remaining composition can also include other carriers such as lactose, glucose, sucrose, salt, cellulose, etc. In specific aspects of the disclosure, the carrier may be 50% or more of the total product.

In certain aspects of the disclosure, the carrier and composition can also have defined properties, such as solubility/insolubility in water or solubility/insolubility in fat, etc.

In certain aspects of the disclosure, other chemicals or materials principally used for the reduction or absorption of moisture may also be included. These may include, but are not limited to: calcium stearate, sodium aluminosilicate, silica, calcium carbonate, zeolite, bicarbonates, sodium sulfate, silicon dioxide, or ascorbic acid.

In certain aspects of the disclosure, other chemicals or materials principally used for the reduction or absorption of oxygen may also be included. These may include, but are not limited to, iron oxides, ascorbic acid, sodium sulfide, and silica materials.

In certain aspects of the disclosure, the biological material mixed with the present carrier can be stored in a pouch or bag fabricated from various materials, a bottle fabricated from a variety of materials, a capsule, a box, or other storage container.

In certain aspects of the disclosure, the biological material mixed in the present carrier may also be used for the application onto a variety of foods including, but not limited to, meats, vegetables, fruits, processed foods, or others.

In certain aspects of the present disclosure wherein formulations are contemplated for preservation, such preservation may include a process of freezing, freeze-drying and/or spray-drying. In certain aspects, the preserved bacteria contain a viable cell concentration of $1 \times 10^8$ to $5 \times 10^{12}$ cfu/g. Still further, in certain aspects the concentrations range from $5 \times 10^{10}$ cfu/g to $5 \times 10^{13}$ cfu/g of bacteria.

In certain instances, a bacterial formulation for administration to a subject or a surface or other target can include a preservation matrix, which contains and preserves the bacterial culture. Such a matrix may include a biologically active binding agent, an antioxidant, a polyol, a carbohydrate and a proteinaceous material. For example, the matrix may have a pH of from about 5.0 to about 7.0. Such a preservation matrix may be capable of maintaining at least about $10^6$ viable cells for a period of at least about 12 months in vitro. In other examples, such a matrix maintains at least about $10^7$ viable cells for a period of at least about 12 months in vitro, and more preferably, at least about $10^8$ viable cells for a period of at least about 12 months in vitro. A preservation matrix may be comprised of ingredients to minimize the damaging effects encountered during the preservation process and to provide functional properties. For example when a *Lactobacillus* strain of the present disclosure is added to a preservation matrix for preservation, it is may converted from an actively growing metabolic state to a metabolically inactive state. In formulations of the present disclosure wherein a preservation matrix is contemplated, a biologically acceptable binding agent can be used to both affix the bacterial culture or cultures to an inert carrier during a preservative process and to provide protective effects (i.e., maintains cell viability) throughout preservation and storage of the microbial cells. Preferred biologically acceptable binding agents for use in a preservation matrix include, but are not limited to a water-soluble gum, carboxymethyl cellulose and/or gelatin. A biologically acceptable binding agent typically comprises from about 10% to about 20% by weight of the preservation matrix, and preferably comprises about 14% by weight of the preservation matrix. In one embodiment, a preservation matrix of the present disclosure comprises about 14% gelatin by weight of the preservation matrix.

Antioxidants included in a preservation matrix may be provided to retard oxidative damage to the microbial cells during the preservation and storage process. A particularly preferred antioxidant is sodium ascorbate. An antioxidant typically comprises from about 0.1% to about 1.0% by weight of the preservation matrix, and preferably comprises about 0.5% by weight of the preservation matrix. In one embodiment, a preservation matrix of the present disclosure comprises about 0.5% sodium ascorbate by weight of the preservation matrix.

Polyols (i.e., polyhydric alcohols) included in a preservation matrix may be provided to maintain the native, uncollapsed state of cellular proteins and membranes during the preservation and storage process. In particular, polyols interact with the cell membrane and provide support during the dehydration portion of the preservation process. Preferred polyols include, but are not limited to xylitol, adonitol, glycerol, dulcitol, inositol, mannitol, sorbitol and/or arabitol. A polyol typically comprises from about 1% to about 25% by weight of the preservation matrix, and preferably comprises about 6% by weight of the preservation matrix. In one embodiment, a preservation matrix of the present disclosure comprises about 6% xylitol by weight of the preservation matrix.

Carbohydrates included in a preservation matrix may be provided to maintain the native, uncollapsed state of cellular proteins and membranes during the preservation and storage process. In particular, carbohydrates provide cell wall integrity during the dehydration portion of the preservation process. Preferred carbohydrates include, but are not limited to dextrose, lactose, maltose, sucrose, fructose and/or any other monosaccharide, disaccharide or polysaccharide. A carbohydrate typically comprises from about 0.5% to about 5% by weight of the preservation matrix, and preferably comprises about 2.5% by weight of the preservation matrix. In one embodiment, a preservation matrix of the present disclosure comprises about 2.5% dextrose by weight of the preservation matrix.

A proteinaceous material included in a preservation matrix may provide further protection of the microbial cell during the dehydration portion of the preservation process. Preferred proteinaceous materials include, but are not limited to skim milk and albumin. A proteinaceous material typically comprises from about 0.5% to about 5% by weight of the preservation matrix, and preferably comprises about 1.5% by weight of the preservation matrix. In one embodiment, a preservation matrix of the present disclosure comprises about 1.5% skim milk by weight of the preservation matrix.

One example of a method of preserving microbial cells within a preservation matrix includes coating the cell matrix suspension onto an inert carrier that preferably is a maltodextrin bead. The coated beads can then be dried, preferably by a fluid bed drying method. Fluid bed drying methods are well known in the art. For example, maltodextrin beads may be placed into a fluid bed dryer and dried at 33° C. The air pressure may be set to 1 bar, the cell suspension matrix can then be sprayed onto the beads and the heat is increased to 38° C. The coated beads are then allowed to dry for an additional period of time. The coated maltodextrin beads can be stored as a powder, placed into gelatin capsules, or pressed into tablets.

In other formulations of the disclosure, the single strains or combinations of strains of bacteria contemplated to be cultured can be formulated as a hard gelatin capsule. Gelatin capsules are commercially available and are well known in the art. In this embodiment, the above preservation method further comprises dispensing the cell suspension matrix to a gelatin capsule, chilling the gelatin capsule until the cell suspension matrix forms a non-fluid matrix and to affix the gel to the interior wall of the gelatin capsule, and desiccating the gelatin capsule in a desiccation chamber. The step of dispensing can be accomplished by any means known in the art, and includes manual, semi-automated and automated mechanisms. The chilling step is performed at from about 4° C. to about 6° C. The step of desiccating the gelatin capsule can include the steps of (i) providing dry air to the desiccation chamber containing less than about 25% moisture, at a temperature from about 24° C. to about 32° C.; and (ii) removing humidified air from the desiccation chamber.

In this formulation of the present disclosure the desiccation process may proceed for about 1 to about 6 hours. The desiccation chamber can include a compressor, at least one hydrocarbon scrubbing filter and a chilled air compressor with or without a desiccant silica gel (or any other suitable desiccant material) column, in series. The air entering the chamber (dry air) preferably contains less than about 25% moisture, and more preferably less than about 15% moisture, and even more preferably less than about 5% moisture, down to as little as zero moisture. The dry air should preferably have a temperature from about 24° C. to about 32° C. This method allows preservation of microbial cells in a controlled environment with room temperature air in a short period of time. Further examples of embodiments of preservation matrices and gelatin capsule formulations may be found in U.S. Pat. No. 6,468,526 which is herein incorporated by reference in its entirety.

In certain applications, the bacteria cultured with the methods described herein may be placed in a microencapsulation formulation. Such microencapsulation formulations may have applicability for example in administration to subjects via oral, nasal, rectal, vaginal or urethral routes. Spray drying is the most commonly used microencapsulation method in the food industry, is economical and flexible, and produces a good quality product. The process involves the dispersion of the core material into a polymer solution, forming an emulsion or dispersion, followed by homogenisation of the liquid, then atomisation of the mixture into the drying chamber. This leads to evaporation of the solvent (water) and hence the formation of matrix type microcapsules.

For example O'Riordan et al., 2001 reported microencapsulation and spray drying of *Bifidobacterium* cells with a spray inlet temperature of 100° C. and low outlet temperature of 45° C. The cells were reported to be encapsulated satisfactorily to produce micro spheres with gelatinized modified starch as a coating material (O'Riordan et al., 2001). In this study, spray drying was found to be a valuable process for encapsulating Bifidobacteria. The process of spray drying is economical, easily scaled up and uses equipment readily available in the food industry (Gibbs et al., 1999). A previous report indicated that survival of probiotic bacteria during spray drying decreased with increasing inlet temperatures (Mauriello et al., 1999).

In one such example of microencapsulation, lyophilized bacteria are suspended in 10 ml of 5% glucose saline solution in a volume so as to obtain a heavy suspension of bacteria which contains approximately $10^9$ organisms per ml, at 0° C. to 4° C. The suspension of bacteria may then be rapidly, but gently, stirred while 0.2-0.4 ml of sodium alginate solution (1.5% weight by volume) is added. The above mixture may then be transferred into a sterile container by using a nitrogen stream through a 14 gauge sheathed needle. The mixture may then be forced through a 30 gauge multi-beveled needle under pressure using a large syringe and nitrogen stream. Very small droplets are generated at the end of the needle, which are then dried by the nitrogen and air stream around the 30 gauge needle, and the droplets are collected in an aqueous solution of 1.3-2% calcium chloride where they gel. Thereafter, they are washed at least three times with 0.08-0.13% 2-(N-cyclohexylamino) ethanesulfonic acid (CHES) solution and 1.0-1.5% calcium chloride solution. The gelled droplets or little spheres are further washed with at least a five-fold excess of the 0.1% CHES 1.1% calcium chloride, and normal saline solution. The resultant spheres are then "snap frozen" in liquid nitrogen and then lyophilized. After these steps, the encapsulated organisms can be used in the formulations of the present disclosure. Other examples of microencapsulation can be found for example in U.S. Pat. No. 5,641,209 that is herein incorporated by reference.

Dry microorganism cultures may be prepared according to the disclosure, in addition to any constituents present from a fermentation medium, such as metabolic products, the medium may comprise at least one matrix material with or without other stabilizing substances. These materials are preferably selected from inorganic salts or buffers, at least one other compound which is selected from mono-, oligo- and polysaccharides, polyols, polyethers, amino acids, oligo- and polypeptides, milk-derived compounds, organic carboxylic acids, mineral compounds, organic carrier materials such as wheat semolina bran, alginates, DMSO, PVP (polyvinylpyrrolidone), CMC (carboxymethylcellulose), alpha-tocopherol, beta.-carotene and mixtures thereof.

Examples of suitable saccharide carrier components are sucrose, fructose, maltose, dextrose, lactose and maltodextrin. An example of a suitable polyol is glycerol. Examples of suitable amino acids are glutamic acid, aspartic acid and the salts thereof. An example of a suitable peptide carrier is peptone. An example of a milk-derived compound is, in addition to the abovementioned maltodextrin, also sweet whey powder. Suitable organic carboxylic acids are, for example, citric acid, malic acid and L-ascorbic acid. Examples of suitable mineral carriers are montmorillonite and palygorskite.

In certain aspects of the disclosure mixtures of the abovementioned classes of substances may be employed. Mixtures of this type preferably comprise, as main component, a matrix material, such as one of the abovementioned saccharide components or, for example, sweet whey powder, with or without a minor content of at least one further component, such as a buffer component (for example citric acid) or an antioxidant (for example L-ascorbic acid or α-tocopherol). The addition of further stabilizing constituents, such as sodium glutamate and/or peptone, has likewise proved to be advantageous.

The matrix component is customarily used in carrier compositions usable according to the disclosure in about 5 to 30 times the amount of the other carrier constituents. Examples of particularly suitable carrier combinations are: a) sweet whey powder/citric acid/L-ascorbic acid (weight ratio about 40:1:1). b) maltodextrin/lactose/citric acid/L-ascorbic acid (weight ratio about 20:20:1:1), unsupplemented or supplemented by about 1.5 parts of beta-carotene and 0.5 part of alpha-tocopherol per part of citric acid. c) maltodextrin/sodium glutamate/L-ascorbic acid (weight ratio about 10:1.5:1). d) lactose/glucose/peptone/citric acid (weight ratio about 6:6:1.2:1).

The carrier substances according to the disclosure can be added to the microorganism suspension either as solid or in dissolved form. However, preferably, a sterile solution of the carrier/carriers is prepared, this is cooled to a temperature of from 4 to 10° C. and this is mixed with the likewise cooled microorganism suspension with gentle stirring. To prepare a homogeneous suspension, the resultant mixture is stirred with further cooling for a period of from about 10 minutes to 1 hour.

The microorganism suspension containing the carrier added in the manner described above can then be dried in various ways. Suitable drying processes are in principle freeze drying, fluidized-bed drying and, preferably, spray-drying. For the purposes of the present disclosure, spray-drying also comprises modified spray-drying processes, such as spray-agglomeration or agglomerating spray-drying. The latter process is also known under the name FSD (fluidized spray-dryer) process.

Freeze-drying for preparing dry microorganism cultures according to the disclosure can be carried out, for example, on the basis of the freeze-drying process described in U.S. Pat. No. 3,897,307. The contents of these publications are hereby incorporated completely by reference.

Another, drying process contemplated for use in the present disclosure is spray-drying. Those methods which can be used according to the disclosure are essentially all spray-drying techniques known in the art. The material to be sprayed can, for example, be dried concurrently or countercurrently; spraying can be carried out by means of a single-component or multiple-component nozzle or by means of an atomizer wheel.

Preference is given according to the disclosure to the use of material to be sprayed having a solids content (after addition of the carrier) of from about 10 to 40, such as from about 10 to 25% by weight.

One particular factor according to the disclosure is the use of preconditioned, i.e. low-moisture, drying air. Preferably, use is made of compressed air having a dew point at about −25° C.

The drying process according to the disclosure may be carried out in such a manner that a very low residual moisture content is present in the dry material. The percentage water content is preferably from about 2 to 3% by weight. This may be achieved by adding a post-drying step subsequently to the spray-drying step. The drying material for this purpose is, for example, post-dried in a fluidized bed, preferably at a temperature in the range of from 15 to 50° C. for a period of, for example, from 15 minutes to 20 hours. Again, preferably, conditioned compressed air or conditioned nitrogen serves as drying gas. However, the post-drying can also be performed by applying a vacuum of from about 1 to 50 mm Hg for a period of from about 15 minutes to 20 hours and at a temperature of from about 15 to 50° C. In this case, preference is given to stirring the drying material, for example, using a paddle agitator.

Instead of the above-described physical post-drying processes, it is also conceivable to add specific desiccants to the dry material obtained from the spray-drying. Examples of suitable desiccants are inorganic salts, such as calcium chloride and sodium carbonate, organic polymers, such as the product obtainable under the trade name Kollidon 90 F, and silicon-dioxide-containing desiccants, such as silica gel, zeolites and desiccants which are obtainable under the trade name Tixosil 38, Sipernat 22 S or Aerosil 200.

The content of viable microorganisms is in the range of from about $5 \times 10^5$ to $1 \times 10^{12}$ cfu/g of dry matter. These preparations are also called according to the disclosure powder concentrates. Since, for individual final applications, lower contents of viable microorganisms are also completely sufficient, powder concentrates of this type can therefore if appropriate be blended to the final count of viable microorganisms by mixing with further inert carrier material.

Some bacteria can survive environmental stresses through the formation of spores. This complex developmental process is often initiated in response to nutrient deprivation. It allows the bacterium to produce a dormant and highly resistant cell. Spores can survive environmental assaults that would normally kill other bacteria. Some stresses that endospores can withstand include exposure to high temperatures, high UV irradiation, desiccation, chemical damage and enzymatic destruction. The extraordinary resistance properties of endospores make them of particular importance because they are not readily killed by many antimicrobial treatments. Common bacteria that form spores include species from the *Bacillus* and *Clostridium* genera. Spores formed by these bacteria remain in their dormant state until the spores are exposed to conditions favorable for growth. The inclusion of spores in a probiotic composition is appealing because of their ability to withstand processing methods and can have extended shelf life viabilities. Additionally, bacterial spores can require less processing because they do not require additional steps for preservation (such as freeze drying, spray drying, freezing, etc.) as is required for many other probiotic organisms.

In still other embodiments of the disclosure, a gel formulation for delivery of probiotic bacteria to animals is used. A gel is defined herein as an apparently solid, jelly-like material formed from a colloidal solution. A colloidal solution is a solution in which finely divided particles which are dispersed within a continuous medium in a manner that prevents them from being filtered easily or settled rapidly. Methods pertaining to the formulation of gels are set forth in U.S. Pat. No. 6,828,308, U.S. Pat. No. 6,280,752, U.S. Pat. No. 6,258,830, U.S. Pat. No. 5,914,334, U.S. Pat. No. 5,888,493, and U.S. Pat. No. 5,571,314, each of which is herein specifically incorporated by reference in its entirety.

d. Uses of Formulated Bacterial Products

The methods and formulations of the present disclosure can be adjusted to provide beneficial effects to many types of animals, including ruminal fermentors, cecal fermentor and intestinal fermentors. In one preferred embodiment, the product is fed to ruminal fermentors to reduce scours events, improve animal health and animal productivity. Ruminal fermentors that might benefit from the present disclosure include but are not limited to: cattle, sheep, goats, camels, llama, bison, buffalo, deer, wildebeest, antelope, and any other pre-gastric fermentor. In another embodiment, the product is fed to cecal fermentors to reduce scours events, improve animal health and animal productivity. Cecal fermentors that might benefit from the present disclosure include but are not limited to: horses, ponies, elephants, rabbits, hamsters, rats, hyraxes, guinea pigs, and any other post-gastric fermentor that using the cecum as the primary location of fermentative digestion. In another embodiment, product is fed to intestinal fermentors to reduce scours events, improve animal health and animal productivity. Intestinal fermentors that might benefit from said disclosure include but are not limited to: humans, pigs, chickens, and other post-gastric fermentor using the large intestine as the primary location of fermentative digestion.

The various embodiments of the disclosure include the application of a combination of probiotic microorganisms to the animal feed. The different microorganisms can be of different species, or they may be of the same species but constitute different strains within. The product may contain multiple species and multiple strains. For example, two, three, four, five, six, and so on different microorganisms and/or strains can be applied. The application of multiple types of different microorganisms and/or different strains lead to additive or more preferably super additive or more preferably synergistic effects in maintaining or improving animal health or decreasing or eliminating the presence of pathogenic bacteria.

The amount of microorganism administered to the animal feed can be any amount sufficient to achieve the desired increase in animal efficiency and/or animal health. This amount can be anywhere from 1 to $10^{13}$ organisms per kg of animal feed. For example, amounts of about $10^4$ cfu/gram feed, about $5 \times 10^4$ cfu/gram feed, about $10^5$ cfu/gram feed, about $5 \times 10^5$ cfu/gram feed, or ranges between 1 to $10^{13}$ organisms per kg of animal feed can be used. In some embodiments, the dried biological may be administered to an animal through a variety of means including, but not limited to, being distributed in an aqueous solution and subsequently being applied to animal feed, water source, or directly fed to the animal, or through direct application of the product onto animal feed or direct administration or consumption by the animal.

In certain embodiments, the microorganisms and methods of the present disclosure involve two or more probiotic bacteria, or in specific embodiments lactic acid-producing bacteria, for the reduction or prevention of scours in calves or for therapeutic benefit to other animals. These compositions would be provided in a combined amount effective to achieve the desired effect, for example, the killing or growth inhibition of a pathogenic microorganism. This process may involve administering different strains or species of lactic acid producing microorganisms at the same time. In certain embodiments the different strains or species may be combined into a single formulation for administration. In other embodiments, the different strains or species of lactic acid producing microorganisms may be each in a single formulation for administration. Still in other embodiments, some lactic acid producing microorganism strains or species may be combined into a single formulation and others may be combined into a different formulation. When more than one formulation is used the formulations may be administered to the animal at the same time or subsequent to each other.

In such instances, it is contemplated that one may administer both formulations within about 12-24 h of each other and, more preferably, within about 6-12 h of each other. In some situations, it may be desirable to extend the time period for administration significantly, however, where several d (2, 3, 4, 5, 6 or 7) to several wk (1, 2, 3, 4, 5, 6, 7 or 8) lapse between the respective administrations.

Various combinations may be employed, for example a formulation containing two species of lactic acid producing microorganisms is "A" and a second formulation containing three species of lactic acid producing microorganisms is "B":

In such embodiments, the administration may be, for example as such: A/B/A, B/A/B, B/B/A, A/B/B, A/B/B, B/A/A, A/B/B/B, B/A/B/B, B/B/B/A, B/B/A/B, A/A/B/B, A/B/A/B, A/B/B/A, B/B/A/A, B/A/B/A, B/A/A/B, A/A/A/B, B/A/A/A, A/B/A/A or A/A/B/A. It is further contemplated that other administrations may be used with three or more different formulations of lactic acid producing microorganisms.

In one embodiment, the novel composition is designed for continual or periodic administration to ruminal fermentors throughout the feeding period in order to reduce the incidence and severity of diarrhea and/or overall health. In this embodiment, the composition comprises a of mixture probiotic microorganisms supplemented with prebiotic substances that can be introduced into the rumen and intestines of a ruminal fermentor. The probiotic microorganisms comprising this embodiment will be those that lead to optimal fermentation and volatile fatty acid production within the gastrointestinal tract of a given ruminal fermentor.

In another embodiment, the novel composition is designed for continual or periodic administration to cecal fermentors throughout the feeding period in order to reduce the incidence and severity of diarrhea and/or overall health. In this embodiment, the composition comprises a mixture of probiotic microorganisms supplemented with prebiotic substances that can be introduced into the cecum and intestines of a cecal fermentor. The probiotic microorganisms comprising this embodiment will be those that lead to optimal fermentation and volatile fatty acid production within the gastrointestinal tract of a given cecal fermentor.

In yet another embodiment, the novel composition is designed for continual or periodic administration to intestinal fermentors throughout the feeding period in order to reduce the incidence and severity of diarrhea and/or overall health. In this embodiment, the composition comprises a mixture of probiotic microorganisms supplemented with prebiotic substances that can be introduced into the intestines of an intestinal fermentor. The probiotic microorganisms comprising this embodiment will be those that lead to optimal fermentation and volatile fatty acid production within the gastrointestinal tract of a given intestinal fermentor.

A wide range of pathogenic bacteria can potentially be inhibited or eliminated through the use of a combination of beneficial probiotic bacteria or microorganisms such as lactic acid producing probiotic bacteria. Specific examples of infectious diseases or conditions of animals which can be caused by pathogenic bacteria include, but are not limited to: staphylococcal infections (caused, for example, by *Staphylococcus aureus, Staphylococcus epidermis*, or *Staphylococcus saprophyticus*), streptococcal infections (caused, for example, by *Streptococcus pyogenes, Streptococcus pneumoniae*, or *Streptococcus agalactiae*), enterococcal infections (caused, for example, by *Enterococcus faecalis*) diphtheria (caused, for example, by *Corynebacterium diptheriae*), anthrax (caused, for example, by *Bacillus anthracis*), listeriosis (caused, for example, by *Listeria monocytogenes*), gangrene (caused, for example, by *Clostridium perfringens*), tetanus (caused, for example, by *Clostridium tetanus*), botulism (caused, for example, by *Clostridium botulinum*), toxic enterocolitis (caused, for example, by *Clostridium difficile*), bacterial meningitis (caused, for example, by *Neisseria meningitidis*), bacteremia (caused, for example, by *Neisseria gonorrhoeae*), *E. coli* infections (colibacilliocis), including urinary tract infections and intestinal infections, shigellosis (caused, for example, by *Shigella* species), salmonellosis (caused, for example, by *Salmonella* species), *Yersinia* infections (caused, for example, by *Yersinia pestis, Yersinia pseudotuberculosis*, or *Yersinia enterocolitica*), cholera (caused, for example, by *Vibrio cholerae*), campylobacteriosis (caused, for example, by *Campylobacter jejuni* or *Campylobacter fetus*), gastritis (caused, for example, by *Helicobacter pylori*), *pseudomonas* infections (caused, for example, by *Pseudomonas aeruginosa* or *Pseudomonas mallei*), *Haemophilus influenzae* type B (HIB) meningitis, HIB acute epiglottitis, or HIB cellulitis (caused, for example, by *Haemophilus influenzae*), pertussis (caused, for example, by *Bordetella pertussis*), mycoplasma pneumonia (caused, for example, by *Mycoplasma pneumoniae*), nongonococcal urethritis (caused, for example, by *Ureaplasma urealyticum*), legionellosis (caused, for example, by *Legionella pneumophila*), syphillis (caused, for example, by *Treponema pallidum*), leptospirosis (caused, for example, by *Leptospira interrogans*), Lyme borreliosis (caused, for example, by *Borrelia burgdorferi*), tuberculosis (caused, for example, by *Mycobacterium tuberculosis*), leprosy (caused, for example, by *Mycobacterium leprae*), actinomycosis (caused, for example, by *Actinomyces* species), nocardiosis (caused, for example, by *Nocardia* species), *chlamydia* (caused, for example, by *Chlamydia psittaci, Chlamydia trachomatis*, or *Chlamydia pneumoniae*), Rickettsial diseases, including spotted fever (caused, for example, by *Rickettsia ricketsii*) and Rickettsial pox (caused, for example, by *Rickettsia akari*), typhus (caused, for example, by *Rickettsia prowazekii*), brucellosis (caused, for example, by *Brucella abortus, Brucella melitens*, or *Brucella suis*), and tularemia (caused, for example, by *Francisella tularensis*). Diseases with similar origins and symptoms are also known to affect animals.

EXAMPLES

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit or scope of the disclosure. The following Examples are offered by way of illustration and not by way of limitation.

Example 1

Preparation of Reagents a. Lactobacilli MRS Agar and Broth

Lactobacilli MRS agar and broth are recommended for the use in the isolation of *Lactobacillus* species. Lactobacilli MRS agar and broth are based on the formulations of de Man et al., *J. Appl. Bacteriol.*, 23:130, 1960. Difco™ & BBL™ Manual, 2nd Edition. The agar and broth were demonstrated by de Man et al., to support Lactobacilli growth from oral, fecal dairy and other sources. Lactobacilli MRS Agar and broth contain peptone and dextrose, both of which supply nitrogen, carbon and other elements necessary for growth. Polysorbate 80, acetate, magnesium and manganese provide growth factors for culturing a variety of lactobacilli.

In brief, to generate Lactobacilli MRS Agar, into one liter of distilled water: 10.0 g proteose peptone No. 3, 10.0 g beef extract, 5.0 g yeast extract, 20.0 g dextrose, 1.0 g polysorbate 80, 2.0 g ammonium citrate, 5.0 g sodium acetate, 0.1 g magnesium sulfate, 0.05 g manganese sulfate, 2.0 g dipotassium phosphate and 15.0 g agar. Lactobacilli MRS broth is generated by the same methods without the addition of agar. These materials are readily obtained from Becton Dickinson and Company, Franklin Lakes N.J.

b. Lactobacilli Fermentation Medium

Lactobacilli fermentation medium may be made by adding into 450 ml of distilled water the following ingredients: 4.0 g trypticase, 3.0 g casamino acids, 6.0 g yeast extract, 0.5 g sodium acetate trihydrate, 1.0 g ammonium citrate, 1.0 g potassium phosphate, 1.0 g magnesium sulfate, 0.05 g manganese sulfate and 500 µA polyoxyethylene (20) sorbitan monooleate.

c. LBS (*Lactobacillus* Selection) Medium

LBS medium may be made by adding into 1 L of distilled water the following ingredients: 10.0 g trypticase, 5.0 g yeast extract, 25.0 g sodium acetate hydrate, 20.0 g glucose, 2.0 g ammonium citrate, 6.0 g monopotassium phosphate, 0.575 g magnesium sulfate anhydrous, 0.12 g manganese sulfate monohydrate, 0.034 g ferrous sulfate, and 1 ml polyoxyethylene (20) sorbitan monooleate. LBS agar may be prepared by adding 15 g of agar to 1 L of the LBS medium.

d. Luria-Bertani Medium

Luria-Bertani (LB) medium may be made by adding into 1 L of distilled water the following ingredients: 10.0 g trypticase, 5.0 g yeast extract, and 10.0 g sodium chloride. LB agar may be prepared by adding 15 g of agar to 1 L of the LB medium.

Example 2 a. Growth Inhibition of *E. coli* by Lactic Acid Producing Bacteria

Tubes containing an MRS medium were inoculated with approximately $1 \times 10^4$ viable cells (based culture optical density) of a selected strain of *E. coli* and $1 \times 10^4$ viable cells (based culture optical density) of the challenging lactic acid bacterium strain. The following species of probiotic lactic acid producing bacteria were used: *Lactobacillus agilis, Lactobacillus agilis, Lactobacillus delbrueckii, Lactobacillus murinus, Lactobacillus plantarum, Lactobacillus reuteri, Lactobacillus salivarius* and *Pediococcus acidilactici*.

Figure 2:
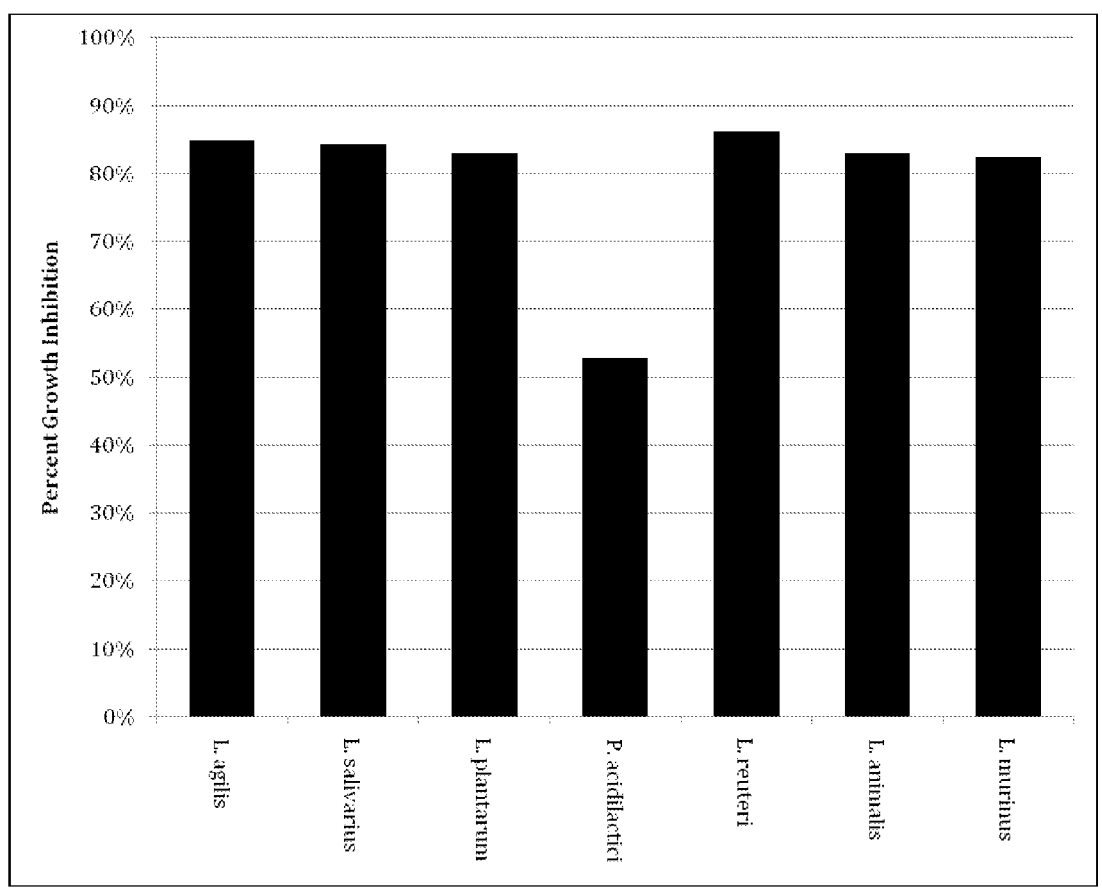
FIG. 2 is a bar graph illustrating the growth inhibition of *E. coli* strain 25922 by various lactic acid producing bacteria.
Figure 3:
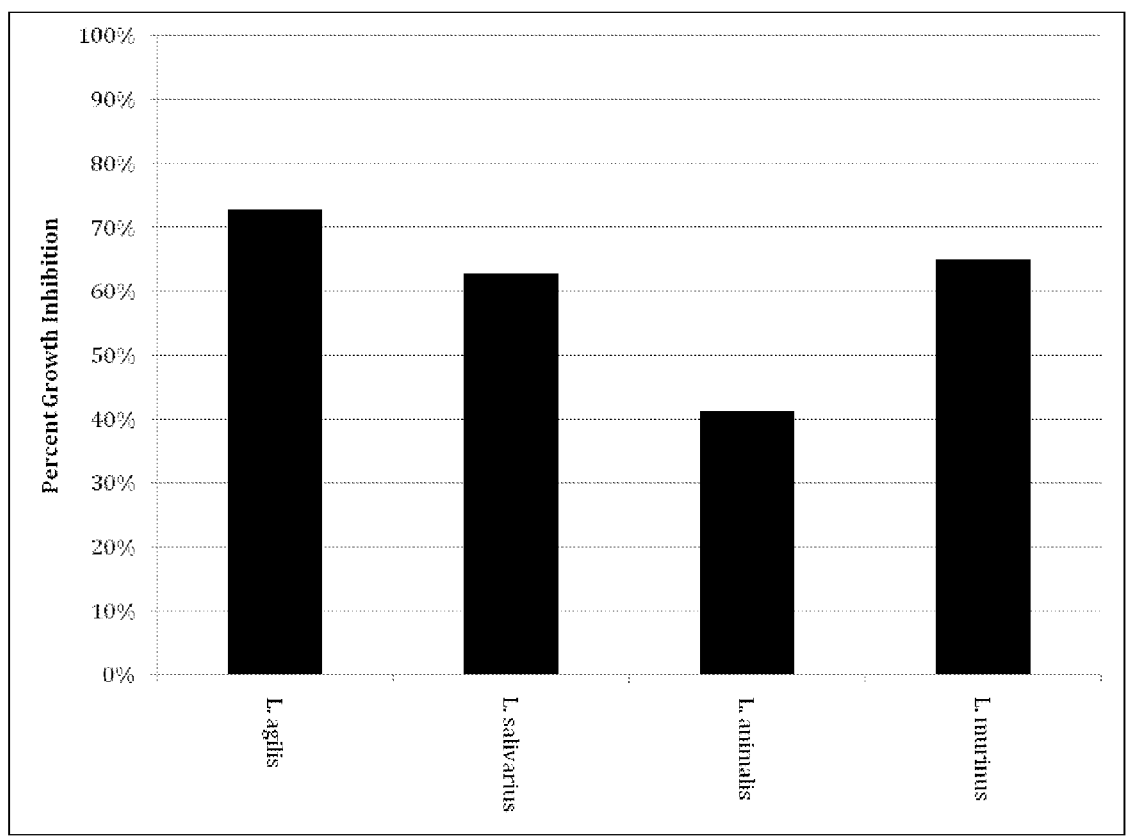
FIG. 3 is a bar graph illustrating the growth inhibition of *E. coli* strain O157:H7 by various lactic acid producing bacteria.

*E. coli* strain 1 was a lab isolate known as CKYL1 and strain 2, available from ATCC was 25922. The third strain was O157:H7. Tubes were then placed into a water bath at 37° C. and incubated for 6 hours. After incubation, tubes were serially diluted and 100 µA spread onto Luria-Bertani plates to enumerate viable *E. coli*. The percent *E. coli* growth inhibition was calculated as the difference in concentration of viable *E. coli* cells in tubes co-incubated with *Lactobacillus* strains from the control *E. coli* viable concentration divided by the concentration of viable *E. coli* incubated without *Lactobacillus* multiplied by 100. Results are shown in Table 1 and FIG. 1 for inhibition of lab strain CKYL1, Table 2 and FIG. 2 for inhibition of lab strain 25922 and Table 3 and FIG. 3 for inhibition of *E. coli* strain O157:H7.

TABLE 1

Growth inhibition of *E. coli* strain CKYL1 by Lactic Acid Producing Bacteria

| LAB Species | Percent *E. coli* Growth Reduced | Ranking |
| --- | --- | --- |
| L. agilis | 81.10% | 3 |
| L. agilis | 75.40% | 4 |
| L. delbrueckii | 12.00% | 6 |
| L. murinus | 87.60% | 2 |
| L. plantarum | 0.00% | 7 |
| L. reuteri | 60.50% | 5 |
| L. salivarius | 93.20% | 1 |
| P. acidilactici | −39.85% | 8 |

TABLE 2

Growth inhibition of *E. coli* strain 25922 by Lactic Acid Producing Bacteria

| LAB Species | Percent *E. coli* Growth Reduced | Ranking |
| --- | --- | --- |
| L. agilis | 84.83% | 2 |
| L. animalis | 82.94% | 4 (t) |
| L. murinus | 82.46% | 6 |
| L. plantarum | 82.94% | 4 (t) |
| L. reuteri | 86.26% | 1 |
| L. salivarius | 84.36% | 3 |
| P. acidilactici | 52.76% | 8 |

TABLE 3

Growth inhibition of *E. coli* strain O157:H7 by Lactic Acid Producing Bacteria

| LAB Species | Percent *E. coli* Growth Reduced | Ranking |
| --- | --- | --- |
| L. agilis | 72.88% | 1 |
| L. animalis | 41.24% | 4 |
| L. murinus | 64.95% | 2 |
| L. salivarius | 62.71% | 3 | b. Growth Inhibition of *Salmonella* by Lactic Acid Producing Bacteria

Tubes containing an MRS medium were inoculated with approximately $1 \times 10^4$ viable cells (based culture optical density) of a selected species of *Salmonella* and $1 \times 10^4$ viable cells (based culture optical density) of the challenging lactic acid bacterium strain. The following species of probiotic lactic acid producing bacteria were used: *Lactobacillus agilis, Lactobacillus agilis, Lactobacillus delbrueckii, Lactobacillus murinus, Lactobacillus plantarum, Lactobacillus reuteri* and *Lactobacillus salivarius*.

Figure 4:
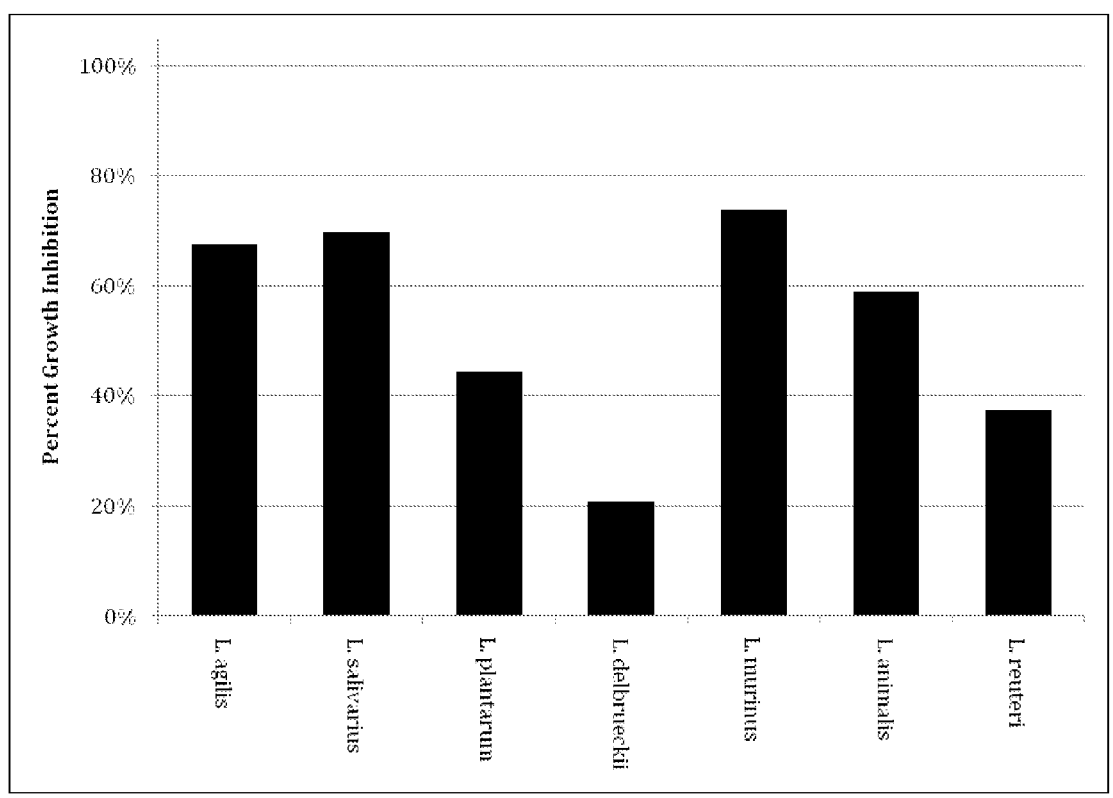
FIG. 4 is a bar graph illustrating the growth inhibition of *Salmonella cholerasuis* by various lactic acid producing bacteria.
Figure 5:
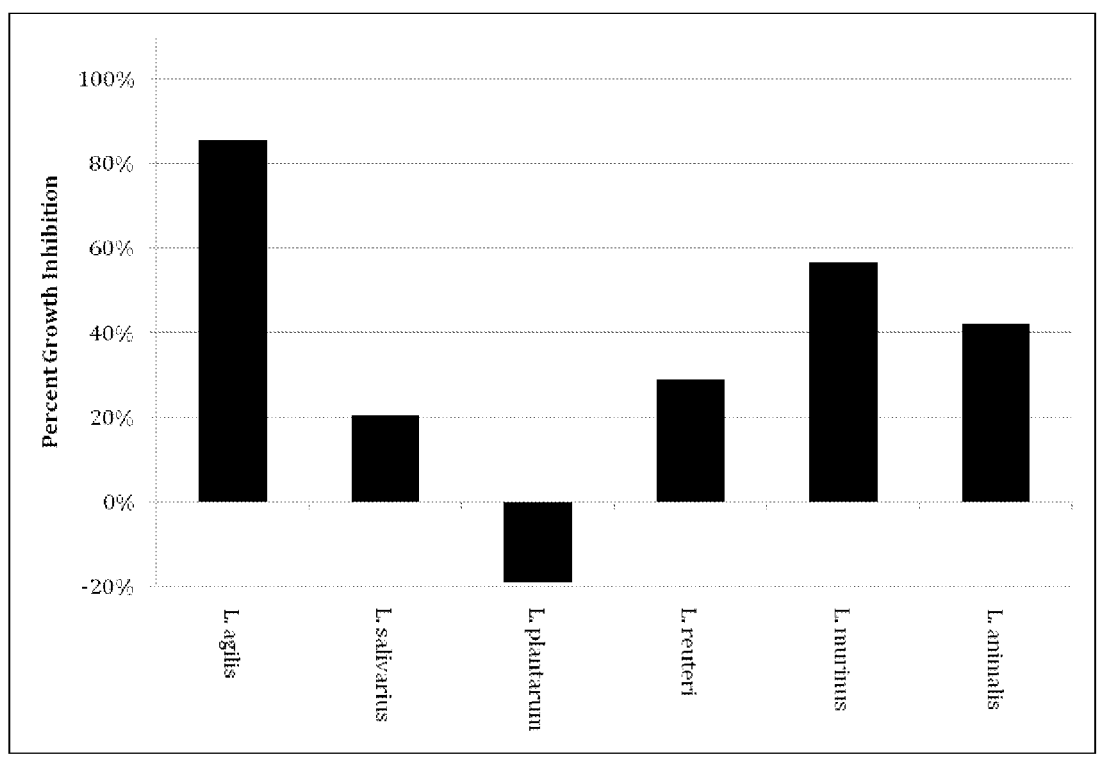
FIG. 5 is a bar graph illustrating the growth inhibition of *Salmonella typhimurium* by various lactic acid producing bacteria.

Two different species of *Salmonella* were used, *Salmonella cholerasuis* and *Salmonella typhimurium*. Tubes were then placed into a water bath at 37° C. and incubated for 6 hours. After incubation, tubes were serially diluted and 100 μl spread onto Luria-Bertani plates to enumerate viable *Salmonella*. The percent *Salmonella* growth inhibition was calculated as the difference in concentration of viable *Salmonella* cells in tubes co-incubated with *Lactobacillus* strains from the control *Salmonella* viable concentration divided by the concentration of viable *Salmonella* incubated without *Lactobacillus* multiplied by 100. Results are shown in Table 4 and FIG. 4 for inhibition of *Salmonella cholerasuis* and Table 5 and FIG. 5 for inhibition of *Salmonella typhimurium*.

TABLE 4

Growth inhibition of *Salmonella cholerasuis* by Lactic Acid Producing Bacteria

| LAB Species | Percent *Salmonella* Growth Reduced | Ranking |
|---|---|---|
| L. agilis | 67.61% | 3 |
| L. animalis | 59.00% | 4 |
| L. delbrueckii | 20.85% | 7 |
| L. murinus | 73.80% | 1 |
| L. plantarum | 44.30% | 5 |
| L. reuteri | 37.50% | 6 |
| L. salivarius | 69.70% | 2 |

TABLE 5

Growth inhibition of *Salmonella typhimurium* by Lactic Acid Producing Bacteria

| LAB Species | Percent *Salmonella* Growth Reduced | Ranking |
|---|---|---|
| L. agilis | 85.54% | 1 |
| L. animalis | 42.17% | 3 |
| L. murinus | 56.60% | 2 |
| L. plantarum | −18.88% | 6 |
| L. reuteri | 29.00% | 5 |
| L. salivarius | 20.40% | 4 | c. Discussion

As shown in Tables 6 and 7 below, the multiple species of lactic acid producing bacteria inhibited the selected strains or species of pathogenic bacteria (*E. coli* and *Salmonella*) at different levels of effectiveness. Thus combining multiple strains of lactic acid producing bacteria may be advisable to provide greater protection and health benefits to animals. Table 6 demonstrates the percentage of inhibition against each pathogenic bacteria studied by selected lactic acid producing bacteria. Likewise, Table 7 demonstrates the relative ranking of the effectiveness of inhibition against each pathogenic bacteria by selected lactic acid producing bacteria.

TABLE 6

Percentage of Inhibition Against Each Pathogenic Bacteria Studied by Selected Lactic Acid Producing Bacteria

| | Pathogen | | | | |
|---|---|---|---|---|---|
| LAB Strain | E. coli (1) | E. coli (2) | E. coli O157:H7 | S. cholerasuis | S. typhimurium |
| L. agilis | 81.10% | 84.83% | 72.88% | 67.61% | 85.54% |
| L. animalis | 75.40% | 82.94% | 41.24% | 59.00% | 42.17% |
| L. delbrueckii | 12.00% | | | 20.85% | |
| L. murinus | 87.60% | 82.46% | 64.95% | 73.80% | 56.60% |
| L. plantarum | 0.00% | 82.94% | | 44.30% | −18.88% |
| L. reuteri | 60.50% | 86.26% | | 37.50% | 29.00% |
| L. salivarius | 93.20% | 84.36% | 62.71% | 69.70% | 20.40% |
| P. acidilactici | −39.85% | 52.76% | | | |

TABLE 7

Ranking of Effectiveness of Inhibition Against Pathogenic Bacteria by Selected Lactic Acid Producing Bacteria

| | Pathogen | | | | |
|---|---|---|---|---|---|
| LAB Strain | E. coli (1) | E. coli (2) | E. coli O157:H7 | S. cholerasuis | S. typhimurium |
| L. agilis | 3 | 2 | 1 | 3 | 1 |
| L. animalis | 4 | 4 (t) | 4 | 4 | 3 |
| L. delbrueckii | 6 | | | 7 | |
| L. murinus | 2 | 6 | 2 | 1 | 2 |
| L. plantarum | 7 | 4 (t) | | 5 | 6 |
| L. reuteri | 5 | 1 | | 6 | 4 |
| L. salivarius | 1 | 3 | 3 | 2 | 5 |
| P. acidilactici | 8 | 8 | | | |

REFERENCES

Baldwin and Allison, *Journal of Animal Science*, 57: (Suppl. 2) 461-477, 1983.
Brashears et al., *Journal of Food Protection*, 66(3):355-363, 2003.
de Man et al., *J. Appl. Bacteriol.*, 23:130
Difco™ & BBL™ Manual, 2nd Edition, Becton Dickinson.
Flint and Angert, *Journal of Microbiological Methods*, 61:235-243, 2005.
Gibbs et al., Int. *J. Food Sci. Nutr.*, 50: 213-224, 1999.
Heilig et al., Applied and Environmental Microbiology, 68:114-123, 2002.
Mauriello et al., *J. Food Prot.*, 62: 773-777, 1999.
O'Riordan et al., *J. Appl. Microbiol.*, 91:1059-1066, 2001.
Radostits et al. Veterinary medicine: a textbook of the diseases of cattle, sheep, pigs, and horses. London: Saunders. 2000.
Roberfroid, M. B., *Am. J. of Clin. Nutr.* 71: 1682S-1687S, 2000.
U.S. Pat. No. 3,897,307
U.S. Pat. No. 4,180,164
U.S. Pat. No. 5,534,271
U.S. Pat. No. 5,529,793
U.S. Pat. No. 5,641,209
U.S. Pat. No. 5,571,314
U.S. Pat. No. 5,888,493
U.S. Pat. No. 5,914,334 U.S. Pat. No. 6,258,830
U.S. Pat. No. 6,280,752 U.S. Pat. No. 6,455,063
U.S. Pat. No. 6,468,526
U.S. Pat. No. 6,828,308 U.S. Pat. No. 6,887,489
U.S. Pat. No. 7,063,836
U.S. Pat. No. 7,323,166
U.S. Publ. Appl. 20070254353

The invention claimed is:

1. A method of reducing growth of pathogenic bacteria in a gastrointestinal tract of an animal comprising providing to an animal at least two administrations of a prepared composition comprising $1 \times 10^{13}$ cfu of *Lactobacillus animalis* probiotic microorganisms per kilogram of feed, wherein when $1 \times 10^4$ viable cells of the *Lactobacillus animalis* probiotic are added to $1 \times 10^4$ viable cells of *Escherichia coli* in a solution of MRS broth in a test tube and incubated in a water bath at 37° C. for six hours, the growth of *Escherichia coli* is reduced by at least 41.24% compared to a preparation of $1 \times 10^4$ viable cells of *Escherichia coli* mixed in a solution of MRS broth in a test tube and incubated in a water bath at 37° C. for six hours without the addition of *Lactobacillus animalis* probiotic.

2. The method of claim 1, wherein when $1 \times 10^4$ viable cells of the *Lactobacillus animalis* probiotic are added to $1 \times 10^4$ viable cells of *Salmonella* in a solution of MRS broth in a test tube and incubated in a water bath at 37° C. for six hours, the growth of *Salmonella* is reduced by at least 42.17% compared to a preparation of $1 \times 10^4$ viable cells of *Salmonella* mixed in a solution of MRS broth in a test tube and incubated in a water bath at 37° C. for six hours without the addition of *Lactobacillus animalis* probiotic.

3. The method of claim 1, wherein the prepared composition further comprises $1 \times 10^{13}$ cfu of *Lactobacillus reuteri* probiotic microorganisms per kilogram of feed, wherein when $1 \times 10^4$ viable cells of the *Lactobacillus reuteri* probiotic are added to $1 \times 10^4$ viable cells of *Escherichia coli* in a solution of MRS broth in a test tube and incubated in a water bath at 37° C. for six hours, the growth of *Escherichia coli* is reduced by at least 60.05% compared to a preparation of $1 \times 10^4$ viable cells of *Escherichia coli* mixed in a solution of MRS broth in a test tube and incubated in a water bath at 37° C. for six hours without the addition of *Lactobacillus reuteri* probiotic.

4. The method of claim 3, wherein when $1 \times 10^4$ viable cells of the *Lactobacillus reuteri* probiotic are added to $1 \times 10^4$ viable cells of *Salmonella* in a solution of MRS broth in a test tube and incubated in a water bath at 37° C. for six hours, the growth of *Salmonella* is reduced by at least 42.17% compared to a preparation of $1 \times 10^4$ viable cells of *Salmonella* mixed in a solution of MRS broth in a test tube and incubated in a water bath at 37° C. for six hours without the addition of *Lactobacillus reuteri* probiotic.

5. The method of claim 1, wherein the prepared composition further comprises $1 \times 10^{13}$ cfu of *Lactobacillus murinus* probiotic microorganisms per kilogram of feed, wherein when $1 \times 10^4$ viable cells of the *Lactobacillus murinus* probiotic are added to $1 \times 10^4$ viable cells of *Escherichia coli* in a solution of MRS broth in a test tube and incubated in a water bath at 37° C. for six hours, the growth of *Escherichia coli* is reduced by at least 64.95% compared to a preparation of $1 \times 10^4$ viable cells of *Escherichia coli* mixed in a solution of MRS broth in a test tube and incubated in a water bath at 37° C. for six hours without the addition of *Lactobacillus murinus* probiotic.

6. The method of claim 5, wherein when $1 \times 10^4$ viable cells of the *Lactobacillus murinus* probiotic are added to $1 \times 10^4$ viable cells of *Salmonella* in a solution of MRS broth in a test tube and incubated in a water bath at 37° C. for six hours, the growth of *Salmonella* is reduced by at least 56.60% compared to a preparation of $1 \times 10^4$ viable cells of *Salmonella* mixed in a solution of MRS broth in a test tube and incubated in a water bath at 37° C. for six hours without the addition of *Lactobacillus murinus* probiotic.

7. The method of claim 1, wherein the prepared composition further comprises $1 \times 10^{13}$ cfu of *Lactobacillus salivarius* probiotic microorganisms per kilogram of feed, wherein when $1 \times 10^4$ viable cells of the *Lactobacillus salivarius* probiotic are added to $1 \times 10^4$ viable cells of *Escherichia coli* in a solution of MRS broth in a test tube and incubated in a water bath at 37° C. for six hours, the growth of *Escherichia coli* is reduced by at least 62.71% compared to a preparation of $1 \times 10^4$ viable cells of *Escherichia coli* mixed in a solution of MRS broth in a test tube and incubated in a water bath at 37° C. for six hours without the addition of *Lactobacillus salivarius* probiotic.

8. The method of claim 7, wherein when $1 \times 10^4$ viable cells of the *Lactobacillus salivarius* probiotic are added to $1 \times 10^4$ viable cells of *Salmonella* in a solution of MRS broth in a test tube and incubated in a water bath at 37° C. for six hours, the growth of *Salmonella* is reduced by at least 42.17% compared to a preparation of $1 \times 10^4$ viable cells of *Salmonella* mixed in a solution of MRS broth in a test tube and incubated in a water bath at 37° C. for six hours without the addition of *Lactobacillus salivarius* probiotic.

9. The method of claim 1, wherein the prepared composition further comprises $1 \times 10^{13}$ cfu of *Lactobacillus agilis* probiotic microorganisms microorganisms per kilogram of feed, wherein when $1 \times 10^4$ viable cells of the *Lactobacillus agilis* probiotic are added to $1 \times 10^4$ viable cells of *Escherichia coli* in a solution of MRS broth in a test tube and incubated in a water bath at 37° C. for six hours, the growth of *Escherichia coli* is reduced by at least 72.88% compared to a preparation of $1 \times 10^4$ viable cells of *Escherichia coli* mixed in a solution of MRS broth in a test tube and incubated in a water bath at 37° C. for six hours without the addition of *Lactobacillus agilis* probiotic.

10. The method of claim 9, wherein when $1\times10^4$ viable cells of the *Lactobacillus agilis* probiotic are added to $1\times10^4$ viable cells of *Salmonella* in a solution of MRS broth in a test tube and incubated in a water bath at 37° C. for six hours, the growth of *Salmonella* is reduced by at least 67.61% compared to a preparation of $1\times10^4$ viable cells of *Salmonella* mixed in a solution of MRS broth in a test tube and incubated in a water bath at 37° C. for six hours without the addition of *Lactobacillus agilis* probiotic.

11. The method of claim 1, wherein the animal is assessed for the presence of pathogenic bacteria in the gastrointestinal tract between administrations.

12. The method of claim 11, wherein the animal is assessed for the presence of pathogenic bacteria by examining feces of the animal for species of pathogenic bacteria, strain of pathogenic bacteria, number of pathogenic bacteria or a combination thereof.

13. The method of claim 1, wherein the administrations are separated by one to seven days.

14. The method of claim 1, wherein the administration is an oral administration.

15. The method of claim 14, wherein the composition is mixed with animal feed.

16. The method of claim 14, wherein the composition is mixed with animal drinking water.

17. The method of claim 1, wherein at least one composition is formulated as a freeze dried formulation.

18. The method of claim 1, wherein the at least two administrations of the prepared composition is to a ruminant animal and the reduction of the growth of pathogenic bacteria is in the post-ruminal digestive tract of the ruminant animal.

19. The method of claim 1, wherein the composition further comprises *Enterococcus faecium, Bacillus licheniformis, Lactococcus lactis, Bacillus subtilis, Bifidobacterium adolescentis, Bifidobacterium animalis, Bifidobacterium bifudum, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus sobrius, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaceus, Streptococcus cremoris, Streptococcus diacetylactis, Streptococcus faecium, Streptococcus intermedius, Streptococcus lactis, Streptococcus thermophilus, Propionibacterium freudenreichii, Propionibacterium acidipropionici, Propionibacterium jensenii, Propionibacterium thoenii, Propionibacterium cyclohexanicum, Propionibacterium granulosum, Propionibacterium microaerophilum, Propionibacterium propionicum, Propionibacterium acnes, Propionibacterium australiense, Propionibacterium avidum* or a combination thereof.

20. A method of reducing growth of pathogenic bacteria in a gastrointestinal tract of an animal comprising providing to an animal an administration of a prepared composition comprising $1\times10^{13}$ cfu of *Lactobacillus animalis* probiotic microorganisms per kilogram of feed prepared from freeze dried *Lactobacillus animalis* having a concentration of $5\times10^5$ to $1\times10^{12}$ cfu per gram of dry matter, wherein when $1\times10^4$ viable cells of the *Lactobacillus animalis* probiotic are added to $1\times10^4$ viable cells of *Escherichia coli* in a solution of MRS broth in a test tube and incubated in a water bath at 37° C. for six hours, the growth of *Escherichia coli* is reduced by at least 41.24% compared to a preparation of $1\times10^4$ viable cells of *Escherichia coli* mixed in a solution of MRS broth in a test tube and incubated in a water bath at 37° C. for six hours without the addition of *Lactobacillus animalis* probiotic.

21. The method of claim 20, wherein when $1\times10^4$ viable cells of the *Lactobacillus animalis* probiotic are added to $1\times10^4$ viable cells of *Salmonella* in a solution of MRS broth in a test tube and incubated in a water bath at 37° C. for six hours, the growth of *Salmonella* is reduced by at least 42.17% compared to a preparation of $1\times10^4$ viable cells of *Salmonella* mixed in a solution of MRS broth in a test tube and incubated in a water bath at 37° C. for six hours without the addition of *Lactobacillus animalis* probiotic.

22. The method of claim 20, wherein the composition further comprises *Enterococcus faecium, Bacillus licheniformis, Lactococcus lactis, Bacillus subtilis, Bifidobacterium adolescentis, Bifidobacterium animalis, Bifidobacterium bifudum, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus,*

*Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus sobrius, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaceus, Streptococcus cremoris, Streptococcus diacetylactis, Streptococcus faecium, Streptococcus intermedius, Streptococcus lactis, Streptococcus thermophilus, Propionibacterium freudenreichii, Propionibacterium acidipropionici, Propionibacterium jensenii, Propionibacterium thoenii, Propionibacterium cyclohexanicum, Propionibacterium granulosum, Propionibacterium microaerophilum, Propionibacterium propionicum, Propionibacterium acnes, Propionibacterium australiense, Propionibacterium avidum* or a combination thereof.

\* \* \* \* \*